(12) United States Patent
Kim

(10) Patent No.: US 11,944,438 B2
(45) Date of Patent: Apr. 2, 2024

(54) SYSTEM FOR DETECTING FEMALE URINATION BY USING WEARABLE DEVICE, AND DIAGNOSIS METHOD USING THE SAME

(71) Applicant: Khaehawn Kim, Gyeonggi-do (KR)

(72) Inventor: Khaehawn Kim, Gyeonggi-do (KR)

(*) Notice: Subject to any disclaimer, the term of this patent is extended or adjusted under 35 U.S.C. 154(b) by 240 days.

(21) Appl. No.: 16/770,263

(22) PCT Filed: Dec. 5, 2018

(86) PCT No.: PCT/KR2018/015324
§ 371 (c)(1),
(2) Date: Jun. 5, 2020

(87) PCT Pub. No.: WO2019/112319
PCT Pub. Date: Jun. 13, 2019

(65) Prior Publication Data
US 2020/0375519 A1    Dec. 3, 2020

(30) Foreign Application Priority Data
Dec. 5, 2017 (KR) .......................... 10-2017-0166099

(51) Int. Cl.
*A61B 5/20*      (2006.01)
*A61B 5/00*      (2006.01)
(Continued)

(52) U.S. Cl.
CPC ................ *A61B 5/202* (2013.01); *A61B 5/01* (2013.01); *A61B 5/1126* (2013.01); *A61B 5/681* (2013.01);
(Continued)

(58) Field of Classification Search
None
See application file for complete search history.

(56) References Cited

U.S. PATENT DOCUMENTS

2016/0120455 A1*   5/2016   Pop ......................... A61F 13/42
                                                                                                       600/301
2016/0310329 A1   10/2016   Patel et al.
(Continued)

FOREIGN PATENT DOCUMENTS

EP           3549519 A1    10/2019
JP        2014-079506 A    5/2014
(Continued)

OTHER PUBLICATIONS

International Search Report for International Application No. PCT/KR2018/015324 dated Apr. 4, 2019.

*Primary Examiner* — Benjamin S Melhus
(74) *Attorney, Agent, or Firm* — Meunier Carlin & Curfman LLC

(57) ABSTRACT

The present disclosure provides a method for detecting female urination by using a wearable device. A female urination detection method according to an embodiment of the present disclosure is a method for detecting urination of a subject to be measured, who is a female, by using a measurement device mounted on the subject to be measured, the method comprising: (a) acquiring sensor data (S) generated according to movement of a sensor of the measurement device; and (b) extracting effective data (SEff) related to urination by filtering the sensor data (S) acquired in (a) by an effective data extracting module of an analysis device through a preset method.

13 Claims, 7 Drawing Sheets

(51) Int. Cl.
*A61B 5/01* (2006.01)
*A61B 5/11* (2006.01)
*G04F 8/00* (2006.01)
*G01P 13/00* (2006.01)

(52) U.S. Cl.
CPC ........ *G04F 8/00* (2013.01); *A61B 2560/0257* (2013.01); *A61B 2562/0219* (2013.01); *A61B 2562/0271* (2013.01); *G01P 13/00* (2013.01)

(56) References Cited

U.S. PATENT DOCUMENTS

| | | | |
|---|---|---|---|
| 2017/0293846 A1 | 10/2017 | Zyglowicz et al. | |
| 2017/0307423 A1* | 10/2017 | Pahwa | G01G 19/18 |
| 2019/0069829 A1* | 3/2019 | Bulut | A61B 5/01 |
| 2019/0142342 A1* | 5/2019 | Nobre | G16H 80/00 |
| | | | 600/301 |

FOREIGN PATENT DOCUMENTS

| | | |
|---|---|---|
| KR | 10-0517820 B1 | 9/2005 |
| KR | 10-2016-0067587 A | 3/2017 |
| KR | 10-2017-0073541 A | 9/2019 |
| WO | 2017104970 A1 | 6/2017 |
| WO | 2017162465 A1 | 9/2017 |
| WO | 2017180661 A1 | 10/2017 |

\* cited by examiner

[FIG. 1]
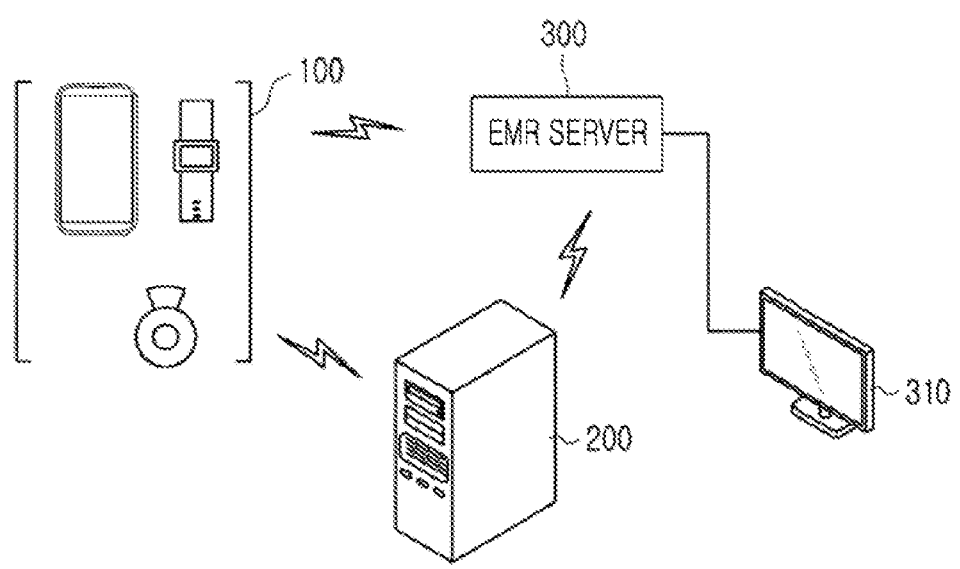

[FIG. 2]
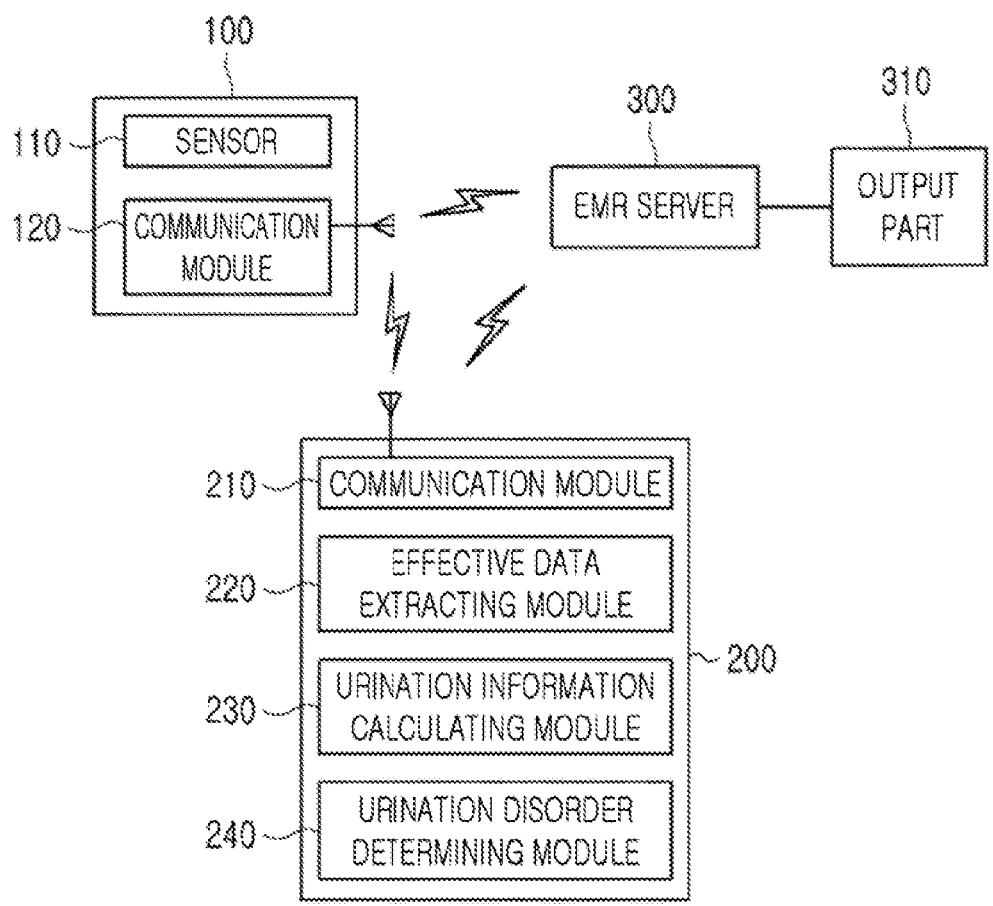

[FIG. 3]
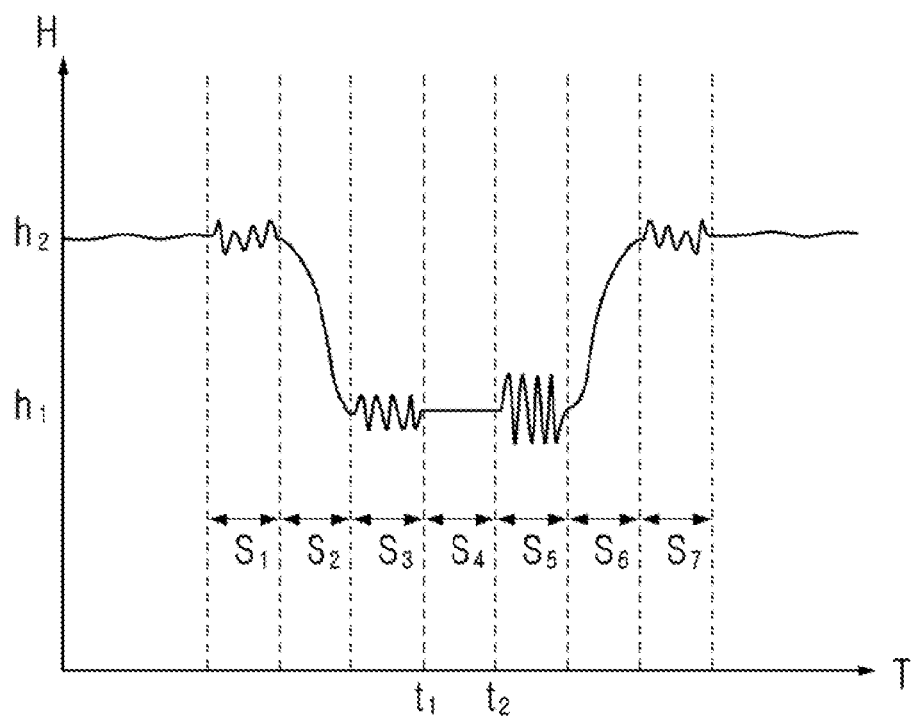

[FIG. 4]
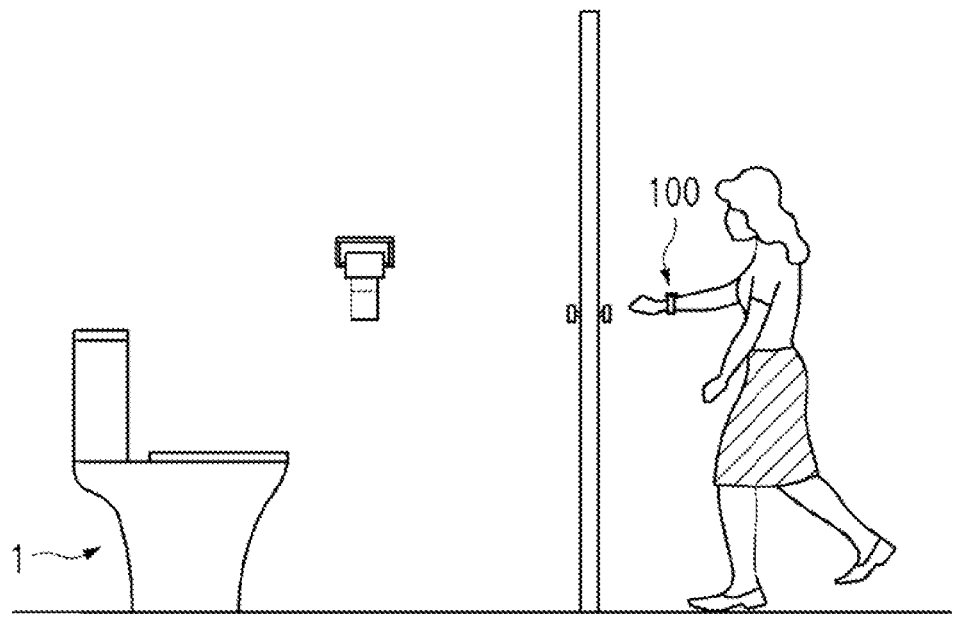
[FIG. 5]
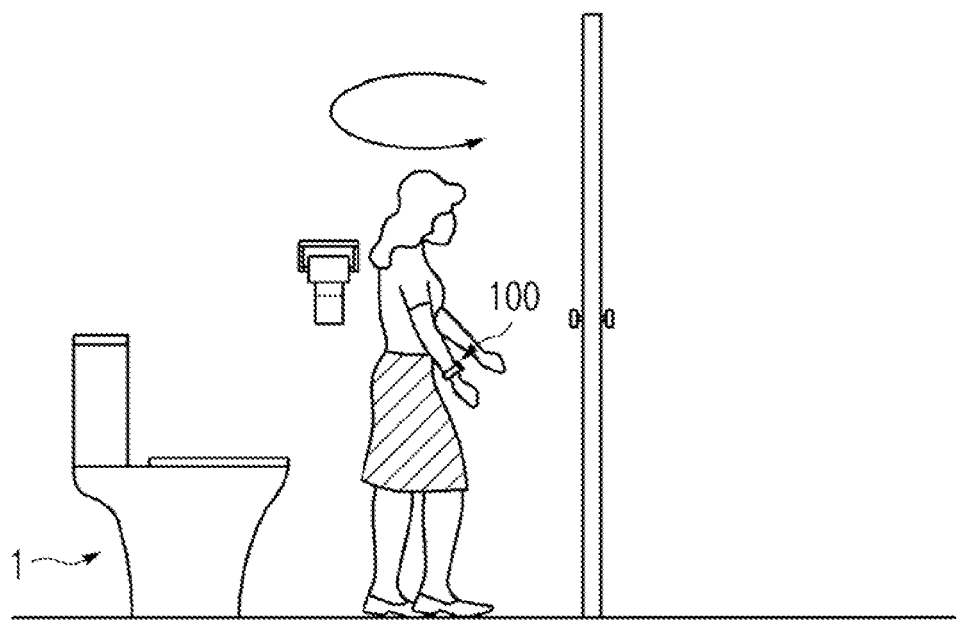

[FIG. 6]
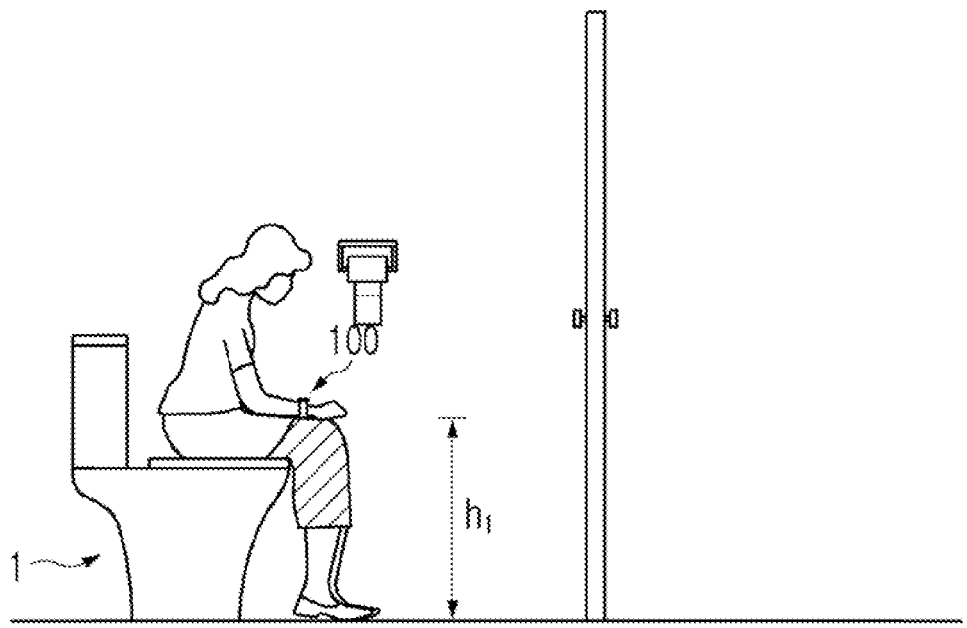

[FIG. 7]
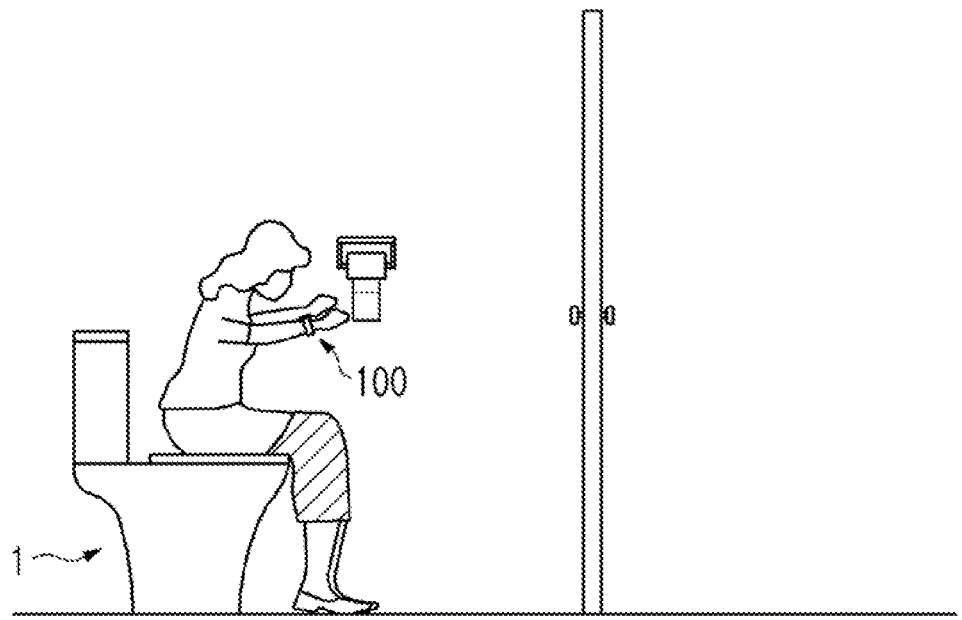
[FIG. 8]
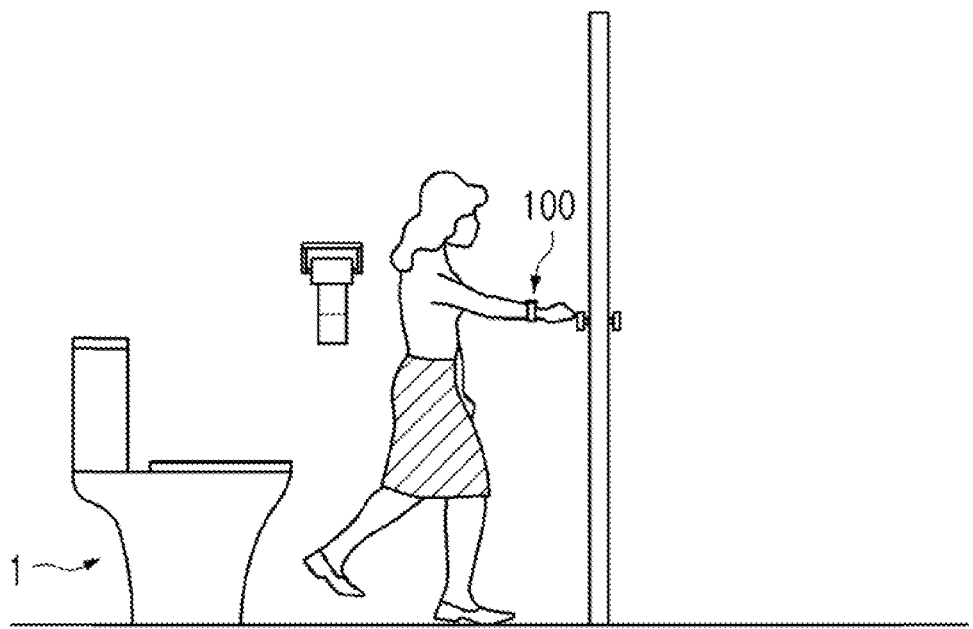

[FIG. 9]
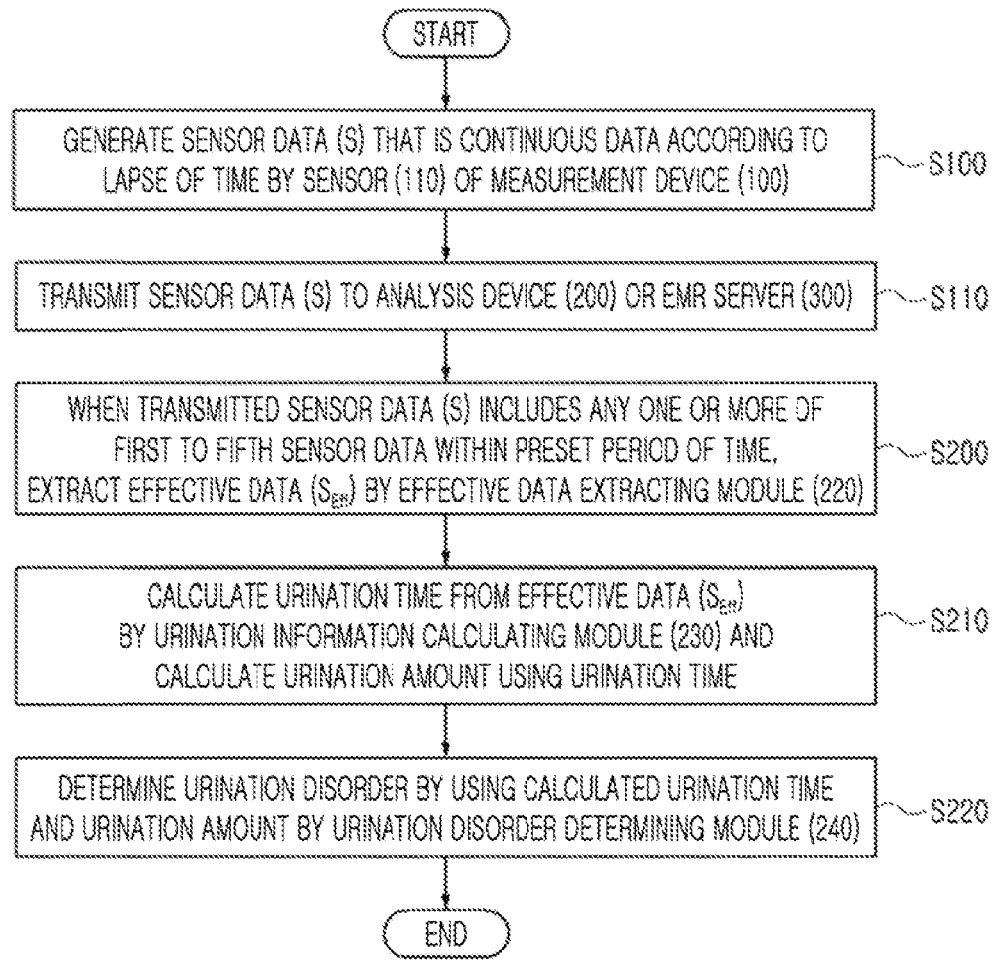

SYSTEM FOR DETECTING FEMALE URINATION BY USING WEARABLE DEVICE, AND DIAGNOSIS METHOD USING THE SAME

CROSS REFERENCE TO RELATED APPLICATION

This is a national stage application of PCT/KR2018/015324 filed Dec. 5, 2018, which claims priority to Korean Patent Application No. 10-2017-0166099, filed Dec. 5, 2017, the contents of which are incorporated herein by reference.

TECHNICAL FIELD

The present disclosure relates to a system for detecting female urination by using a wearable device, and a diagnosis method using the same.

BACKGROUND ART

The disorders related to urination may include difficulties in urination, urinary retention, delayed urination, frequent urination, nocturia, and post-void dribbling. In particular, a delayed urination symptom and a post-void dribbling symptom are commonly found in the elderly, and their causes may be cystitis, and may be various since it may be acute urinary retention, etc., especially for women.

However, it is difficult to identify the delayed urination symptom or the post-void dribbling symptom unless patients reveal the symptoms themselves. In general, the symptoms can be identified by asking an existing patient about his or her condition or using daily record for urination which is a urine check list written by a patient.

However, it is troublesome for the patient to write the daily record and it is difficult to identify whether the check marks are accurately recorded by the patient.

Accordingly, in order to resolve such troublesomeness, there is an increasing demand for a system that can determine urination information and a urination disorder using the urination information by detecting a urination pattern using a wearable device which is mounted on a human body all the time.

(Patent Document 1) Japanese Patent Application Publication No. 2014-79506 (May 8, 2014)
(Patent Document 2) Korean Patent Application Publication No. 10-2017-0073541 (Jun. 28, 2017)

DISCLOSURE

Technical Problem

The present disclosure has been made in an effort to resolve the problems described above. Specifically, the present disclosure provides a urination detection system, which can observe sensor data generated by the movement of a sensor during urination of a female, and which can calculate urination information and determine a urination disorder by extracting effective data.

Technical Solution

According to an embodiment of the present disclosure for resolving the problems described above, there is provided a method for detecting female urination by using a wearable device, wherein the method detects urination of a subject to be measured, who is a female, by using a measurement device 100 mounted on the subject to be measured, the method including: (a) acquiring sensor data S generated according to movement of a sensor 110 of the measurement device 100; and (b) extracting effective data $S_{Eff}$ related to urination by filtering the sensor data S acquired in (a) by an effective data extracting module 220 of an analysis device 200 through a preset method.

According to an embodiment, the sensor data S may be data which is continuous according to lapse of time.

According to an embodiment, (b) may include: extracting effective data $S_{Eff}$ when the sensor data S acquired in (a) includes all of first sensor data $S_1$, which is acquired when the sensor 110 is rotated by a preset angle or more, and second sensor data $S_4$, which is acquired when the sensor 110 is stopped for a preset period of time or more, within a preset period of time.

According to an embodiment, the method may further include: after (b), (c) calculating, among the second sensor data $S_4$ of the extracted effective data $S_{Eff}$, data at an initial time point, at which the sensor 110 is stopped, as a urination start time point $t_1$ and calculating data at a time point, at which the sensor 110 is moved after the urination start time point $t_1$, as a urination end time point $t_2$, by a urination information calculating module (230) of the analysis device (200).

According to an embodiment, (b) may include: extracting effective data $S_{Eff}$ when the sensor data S acquired in (a) includes all of the first sensor data $S_1$, the second sensor data $S_4$, third sensor data $S_2$, which is acquired when the sensor 110 is moved from a preset second height $h_2$ to a first height $h_1$ which is lower than the second height $h_2$, and fourth sensor data $S_6$, which is acquired when the sensor 110 is moved from the first height $h_1$ to the second height $h_2$, within the preset period of time.

According to an embodiment, the first height $h_1$ may be a height corresponding to the height of a knee of a subject to be measured, on which the measurement device 100 is mounted, from the ground.

According to an embodiment, (b) may include: extracting effective data $S_{Eff}$ when the sensor data S acquired in (a) includes all of the first sensor data $S_1$, the second sensor data $S_4$, the third sensor data $S_2$, the fourth sensor data $S_6$, and fifth sensor data $S_5$, which is data that oscillates with a preset amplitude or more, within the preset period of time.

According to an embodiment, the sensor data S may be acquired in the sequence of the first sensor data $S_1$, the third sensor data $S_2$, the second sensor data $S_4$, and the fourth sensor data $S_6$.

According to an embodiment, (c) may include: calculating a difference between the urination end time point $t_2$ and the urination start time point $t_1$ as a urination time and calculating a urination amount through a preset method by using the urination time, by the urination information calculating module 230, and wherein the method may further include: after (c), (d) determining a urination disorder by a urination disorder determining module 240 of the analysis device 200 through a preset method by using a urination time and a urination amount calculated by the urination information calculating module 230.

According to an embodiment, (d) may include: diagnosing a delayed urination symptom by the urination disorder determining module 240 when the urination time is longer than a preset first period of time.

According to an embodiment, the sensor data S may further include temperature data detected by the sensor 110, and (b) may include: extracting effective data $S_{Eff}$ when the sensor data S acquired in (a) includes all of the first sensor data $S_1$, the second sensor data $S_4$, the third sensor data $S_2$, the fourth sensor data $S_6$, and data in which numerical values of the temperature data increase during a time when the third sensor data $S_2$ is acquired, within the preset period time.

According to an embodiment, the preset angle may be 100 degrees.

In addition, the present disclosure provides a computer readable recording medium in which a computer program for executing the method described above is recorded.

In addition, the present disclosure provides a system for detecting female urination by using a wearable device, wherein the system is for performing the method described above, the system including: the measurement device 100 which is mounted on the subject to be measured and in which the sensor 110 configured to generate sensor data S corresponding to movement of the subject to be measured is installed; and the analysis device 200 configured to receive the sensor data S and extract effective data $S_{Eff}$ by filtering the sensor data S through a preset method, and determine a urination disorder by using the effective data $S_{Eff}$.

According to an embodiment, the system may further include: an electronic medical record EMR server 300, to which a urination time and a urination amount calculated by a urination information calculating module 230 of the analysis device 200 are transmitted.

According to an embodiment, a urination disorder determining module 240 of the analysis device 200 may be connected to the EMR server to determine a urination disorder.

According to an embodiment, a unique identifier may be stored in the measurement device 100, and a urination time and a urination amount calculated by the urination information calculating module 230 may be transmitted to the EMR server 300 together with the unique identifier.

According to an embodiment, the sensor 110 may include any one or more of a gyro sensor, an atmospheric pressure detecting sensor, and a temperature sensor.

Advantageous Effects

The present disclosure as described above has the following effects.

First, since only data related to urination are extracted as effective data by filtering sensor data acquired by a sensor, the reliability of the calculated urination information is improved by using the extracted effective data which is data actually related to urination.

Second, since the user can accurately recognize his or her urination data while not feeling excessive inconvenience or not being forced to perform complicated procedures, and thus, the present disclosure can be helpful in diagnosis and treatment of a symptom.

Third, since medical staff can accurately receive patient's daily urination data and diagnose a delayed urination symptom, etc., based on a general reference by using the received data, an accurate diagnosis can be made regardless of skillfulness.

Fourth, since such data may be recorded in an EMR server of a hospital, all data can be identified in real time in the hospital while a patient comfortably stays home. Therefore, such data can be accumulated and shared, thereby securing big data which is useful in medical technologies.

DESCRIPTION OF THE DRAWINGS

FIGS. 1 and 2 are schematic views of a detection system according to an embodiment of the present disclosure;

FIG. 3 is a graph illustrating an example of sensor data generated according to lapse of time when a subject to be measured (i.e., female) urinates;

FIGS. 4 to 8 are schematic views illustrating an appearance of a subject to be measured (i.e., female) upon urination; and FIG. 9 is a flowchart illustrating a detection method according to an embodiment of the present disclosure.

BEST MODE

Hereinafter, the present disclosure will be described in detail with reference to the accompanying drawings.

In particular, it is noted that a "system" means an object that is built according to the present disclosure and is not a method.

In particular, an "EMR" means an electronic medical record and a member that processes information related thereto is referred to as an "EMR server".

1. Description of Detection System

Hereinafter, a detection system according to an embodiment of the present disclosure will be described in detail with reference to FIGS. 1 to 8.

Referring to FIG. 1, a detection system according to an embodiment of the present disclosure includes a measurement device 100, an analysis device 200, and an EMR server 300.

The measurement device 100 is a part that is mounted on a subject to be measured, and may be a device, such as a smart watch, a smart band, a smart ring, a smartphone, other mobile phones, a PDA, etc., which is mounted on the subject to be measured or is used while being attached to a site that is close to a human body.

In addition, the measurement device 100 may be a digital device having a calculation capacity by being equipped with a memory means and a microprocessor.

The measurement device 100 includes a sensor 100 and a communication module 120, and a unique identifier is stored in the measurement device 100. The unique identifier may be an indicator that corresponds to a subject to be measured, on which the measurement device 100 is mounted.

The sensor 110 generates continuous data according to lapse of time. The sensor 110 may be a concept that includes any one or more of a gyro sensor, an atmospheric pressure detecting sensor, a temperature sensor, or all of the above-listed sensors.

The gyro sensor generates sensor data for 3-axis rotation, etc. The atmospheric pressure detecting sensor detects the atmospheric pressure and generates sensor data for a height, at which the sensor is spaced apart from the ground (because the atmospheric pressure decreases as the height increases, the sensor data for the height may be generated), and the temperature sensor generates temperature data for the temperature of a subject to be measured, on which the measurement device 100 is mounted.

The sensor 110 generates sensor data S, which is continuous according to lapse of time, and temperature data, thereby including all data generated in daily life, which is irrelevant to urination, as well as the data related to urination.

Accordingly, a process of extracting only data related to urination is necessary. Hereinafter, sensor data used for extracting effective data $S_{Eff}$ by filtering sensor data S will be described in detail with reference to FIG. 3.

Prior to this, a urination pattern will be discussed with reference to FIGS. 4 to 8 by using an example of a subject to be measured (i.e., female) wearing a measurement device 100 in the form of a smart watch.

The subject to be measured, who entered the bathroom by opening the door, rotates her body in order to sit on a toilet 1 (see FIG. 5). Although it depends on arrangement of the toilet, in general, the subject to be measured rotates her body by 100 degrees or more.

Next, she urinates after disrobing her bottoms and sitting on the toilet 1 (see FIG. 6). In particular, the important thing is that the urine stored in the bladder may be discharged to the outside only when the muscles around the urethra are relaxed. The subject to be measured stops without movement in order to relax the muscles around the urethra. That is, there occurs no movement of the subject to be measured for the period of time for urination, and the sensor 110 generates second sensor data corresponding to $S_4$ of FIG. 3. Since sensor data, in which movement of the subject to be measured is absent, may be arbitrarily observed in daily life, it is preferable that the second sensor data $S_4$ is data continuous for a preset period of time or more. In particular, the present period of time may be understood as a urination time.

When the subject to be measured sits on the toilet 1, the height, at which the measurement device 100 is spaced apart from the ground, becomes lower than that in a standing position. Assuming that the height before sitting on the toilet 1 is a second height $h_2$, when the subject to be measured sits on the toilet 1, the measurement device 100 is located at a first height $h_1$ which is lower than the second height $h_2$. That is, the measurement device 100 generates third sensor data corresponding to $S_2$ when the subject to be measured sits on the toilet 1. The hands of the subject to be measured should be positioned from the height of the waist to the lower side of the knees in order to disrobe the bottoms as well as to be seated. Therefore, changing the height of the measurement device 100 from the second height $h_2$ to the first height $h_1$ may be regarded as a bottom disrobing process.

There may be various methods for detecting the height of the measurement device 100 by the sensor 110. For example, the height may be detected according to a change in atmospheric pressure by providing the sensor 110 with an atmospheric pressure detecting sensor that detects the atmospheric pressure. Since the atmospheric pressure decreases as the height increases, the height may be detected by using this principle.

In particular, it is preferable that the first height $h_1$ is a height from the ground to the knees of the subject to be measured. As a result of analyzing urination postures, for women, there are many cases where they urinate after placing their hands on the thighs (see FIG. 6). In this case, the measurement device 100 mounted on the subject to be measured is also located on the same height as the height of the knees, and thus, sensor data corresponding to the first height $h_1$ may be observed.

In addition, since the body temperature decreases as the skin is exposed to the outside when the bottoms are disrobed, and since the body temperature also decreases after the subject to be measured urinates, a phenomenon in which the body temperature temporarily rises due to shaking or contraction of the muscles occurs physiologically in order to prevent the body temperature from dropping. The sensor 110 including a temperature sensor may generate temperature data corresponding to the temperature of the subject to be measured, and may extract effective data $S_{Eff}$ when data, in which the numerical values of the temperature data increase, are generated.

Next, after urinating, the subject to be measured should separate a part of toilet paper from the roll paper installed on the wall surface of the bathroom in order to wipe her private part. In order to obtain several sheets of toilet paper, the subject to be measured repeats an operation of pulling down the roll paper and rolling it up again. The measurement device 100 mounted on the wrist of the subject to be measured may understand the operation as vertical vibrations having a predetermined amplitude. That is, fifth sensor data corresponding to $S_5$ of FIG. 3 is generated. In particular, the predetermined amplitude may be larger than an amplitude which may be generated in daily life of the subject to be measured.

Next, the subject to be measured puts on the bottoms and stands up from the seating posture. In particular, the height of the measurement device 100 will be located at the second height h2 again, and the measurement device 100 generates fourth sensor data corresponding to $S_6$ of FIG. 3.

The communication module 120 transmits sensor data S generated by the sensor 110 to a communication module 210 of the analysis device 200.

The analysis device 200 is a part that receives sensor data S from the measurement device 110, extracts effective data $S_{Eff}$, and determines a urination disorder by using the effective data $S_{Eff}$. The analysis device 200 may be a digital device having a calculation papacity by being equipped with a memory means and a microprocessor.

Referring to FIG. 2, the analysis device 200 includes a communication module 210, an effective data extracting module 220, a urination information calculating module 230, and a urination disorder determining module 240.

The communication module 210 is a part that receives sensor data S from the communication module 120 of the measurement device 100.

The effective data extracting module 220 is a part that extracts effective data $S_{Eff}$ related to urination by filtering the sensor data S.

Specifically, the effective data extracting module 220 determines whether the sensor data S are effective data $S_{Eff}$ related to urination through a combination of the first sensor data to fifth sensor data, and data, in which the numerical values of the temperature data increase.

Even when any one of the data described above is included, it may be extracted as the effective data $S_{Eff}$, and when two kinds of data are included, they may be extracted as the effective data $S_{Eff}$, and when all the data are included, they may be extracted as the effective data $S_{Eff}$. It is apparent that the precision of extraction improves as the number of the kinds of data, which are included in order to extract the effective data $S_{Eff}$, increases.

In particular, the important thing is that the data used for extraction should be acquired within a preset period of time. Since the sensor data S is continuous data according to lapse of time, only the data acquired for the preset period of time may be regarded as the effective data related to urination.

The urination information calculating module 230 is a part that calculates, among the second sensor data $S_4$ of the effective data $S_{Eff}$ extracted by the effective data extracting module 220, the data at an initial time point, at which the sensor 110 is stopped, as a urination start time point $t_1$, and calculates the data at a time point, at which the sensor 110 is moved after the urination start time point $t_1$, as a urination end time point $t_2$.

In addition, a difference between the urination end time point $t_2$ and the urination start time point $t_1$ may be calculated as a urination time, and a urination amount may be calculated by using the urination time. In particular, the urination amount may be calculated by multiplying the urination time and a urination speed, and more specifically, may be calculated by multiplying the urination time and a number of 25 to 30. This is based on a statistical value, in which a normal female urinates at a speed of 25 to 30 mL/sec.

The urination disorder determining module 240 is a part that determines a urination disorder by using a urination time and a urination amount calculated by the urination information calculating module 230.

Specifically, the urination disorder determining module 240 may diagnose a delayed urination symptom when the urination time is longer than a preset first period of time. In particular, the preset first period of time may be 30 seconds.

As described below, the urination disorder determining module 240 may be connected to the EMR server 300 to determine a urination disorder.

The EMR server 300 is a part that may receive sensor data S and a unique identifier from the measurement device 100 and may receive a urination time and a urination amount from the analysis device 300.

Any EMR server that is conventionally widely used may be used as the EMR server 300. However, the received data can be accurately recorded and maintained only when the unique identifier received from the measurement device 100 is stored.

The urination disorder determining module 240 of the analysis device 200 may be connected to the EMR server 300 to determine a urination disorder by using the urination time and the urination amount stored in the EMR server 300, and may output the urination time and the urination amount to an output part 310 according to the determination result for a urination disorder.

2. Description of Detection Method

Hereinafter, a detection method according to an embodiment of the present disclosure will be described in detail with reference to FIG. 9.

First, the sensor 110 of the measurement device 100 mounted on the subject to be measured generates sensor data S that is continuous according to lapse of time (S100) (see FIG. 3).

Next, the sensor data S are transmitted to the analysis device 200 or the EMR server 300. As described above, the urination information calculating module 230 of the analysis device 200 may calculate a urination time and a urination amount by using the sensor data S directly transmitted to the analysis device 200, but it is apparent that the urination information calculating module 230 is directly connected to the EMR server 300 to calculate the urination information.

Next, the effective data extracting module 220 of the analysis device 200 extracts effective data $S_{\mathit{Eff}}$ when the transmitted sensor data S includes any one or more of the first sensor data to fifth sensor data, and the data, in which the numerical values of the temperature data increase, within a preset period of time.

The first sensor data to fifth sensor data, and the data, in which the numerical values of the temperature data increase, may be data generated when the subject to be measured urinates. That is, when the sensor data S includes any one or more of the data described above within a preset period of time, it may be determined that the subject to be measured is urinating, and this is extracted as the effective data $S_{\mathit{Eff}}$. It is apparent that the possibility of the data extracted as the effective data $S_{\mathit{Eff}}$ being data during urination becomes higher as the number of the data that should be included in the sensor data S to extract the effective data $S_{\mathit{Eff}}$ increases.

Next, the urination information calculating module 230 calculates a urination time from the effective data $S_{\mathit{Eff}}$ and calculates an urination amount by using the urination time (S210). The method for calculating the urination time and the urination amount from the effective data $S_{\mathit{Eff}}$ has been described above, and a detailed description thereof will be omitted.

Next, the urination disorder determining module 240 determines a urination disorder by using the urination time and the urination amount, which have been calculated (S220). For example, when the urination time is longer than a preset first period of time, a delayed urination symptom may be diagnosed. In particular, the preset first period of time may be 30 seconds.

In this way, the determined urination disorder may be transmitted to the measurement device 100 or the EMR server 300, thereby having an advantage in that the subject to be measured or the medical staff can diagnose the heath state of an individual in real time.

Although the embodiments illustrated in the drawings have been described in the specification for reference such that a person skilled in the art can easily understand and realize the present disclosure, they are merely exemplary and a person skilled in the art can understand that various modifications and equivalent embodiments are also made from the embodiments of the present disclosure. Accordingly, the scope of the present disclosure should be determined by the claims.

DESCRIPTION OF REFERENCE NUMERALS

1: toilet
100: measurement device
110: sensor
120: communication module
200: analysis device
210: communication module
220: effective data extracting module
230: urination information calculating module
240: urination disorder determining module
300: EMR server
310: output part

The invention claimed is:

1. A method for detecting female urination, the method comprising:
(a) providing a wearable measurement device, wherein the wearable measurement device detects urination of a female subject, said wearable measurement device comprising a sensor and a communications module;
(b) mounting the wearable measurement device on the female subject, wherein the wearable measurement device is mounted on a wrist of the female subject;
(c) acquiring sensor data generated according to a movement of the sensor of the wrist-worn wearable measurement device, said sensor comprising a first sensor and a second sensor, said first sensor comprising a gyro sensor and said second sensor comprising an atmospheric pressure detecting sensor, and wherein the sensor data comprises 3-axis rotation data from the first sensor and height data from the second sensor defining a height at which the second sensor is spaced apart from the ground, said movement comprises a bottom disrobing process where the female subject changes the height of the sensor from a second height which is a standing height to a first height which is lower than the standing height, and said movement further comprising vertical vibrations having a predetermined amplitude measured by the first sensor and/or the second sensor of the wrist-worn wearable measurement device, said vertical vibrations having the predetermined amplitude providing an indication of a urination end time point;

(d) transmitting the sensor data from the wrist-worn wearable measurement device to an analysis device using the communications module of the wrist-worn wearable measurement device, said analysis device comprising a memory and a microprocessor;

(e) extracting, by the analysis device, effective data related to the urination of the female subject by filtering the sensor data obtained from the wrist-worn wearable measurement device, said analysis device configured to receive, and process the sensor data to determine the effective data through a first preset method;

(f) determining one or more of a urination start time point, the urination end time point, a urination time, a urination amount, a urination disorder, and a delayed urination symptom of the female subject using the effective data related to the urination of the female subject, by the analysis device;

(g) transmitting at least the urination time, the urination amount, and the determined urination disorder calculated by the analysis device to an electronic medical record (EMR) server connected to the analysis device, said EMR server comprising an output part; and (h) outputting at least the urination time, the urination amount, and the urination disorder using the output part, wherein a unique identifier is stored in the wrist-worn wearable measurement device, and wherein the EMR server is configured to receive the transmission of the urination time, the urination amount, and the determined urination disorder calculated by the analysis device together with the unique identifier.

2. The method of claim 1, wherein the sensor data is data which is continuous according to a lapse of time.

3. The method of claim 2, wherein extracting, by the analysis device, the effective data related to the urination of the female subject comprises filtering all of the sensor data to determine when the first sensor is rotated by a preset angle or more, and to determine when the first sensor is stopped for a preset period of time or more during the lapse of time.

4. The method of claim 3, further comprising:
calculating, an initial time point at which the first sensor is stopped as the urination start time point and calculating a second time point, at which the first sensor is moved after the urination start time point, as the urination end time point, by the analysis device.

5. The method of claim 4, wherein extracting, by the analysis device, the effective data related to the urination of the female subject further comprises:
filtering the sensor data obtained from the wrist-worn wearable measurement device to determine when the second sensor is moved from the second height to the first height which is lower than the second height, and to determine when the second sensor is moved from the first height to the second height, during the lapse of time.

6. The method of claim 5, wherein the first height is a height corresponding to a height of a knee of the female subject to be measured from the ground.

7. The method of claim 5, wherein extracting, by the analysis device, the effective data related to the urination of the female subject further comprises:
filtering the sensor data obtained from the wrist-worn wearable measurement device to determine data from the first sensor or the second sensor that oscillates with a preset amplitude or more, during the lapse of time.

8. The method of claim 7, wherein the sensor data obtained from the wrist-worn wearable measurement device is acquired in a sequence of determining when the first sensor is rotated by a preset angle or more, determining when the second sensor is moved from the second height to the first height which is lower than the second height, determining when the first sensor is stopped for the preset period of time or more, and determining when the second sensor is moved from the first height to the second height, during the lapse of time.

9. The method of claim 4, wherein calculating, the initial time point at which the first sensor is stopped as the urination start time point and calculating the second time point, at which the first sensor is moved after the urination start time point, as the urination end time point, by the analysis device, comprises:
calculating a difference between the urination end time point and the urination start time point as the urination time and calculating the urination amount through a second preset method by using the urination time, by the analysis device, and wherein the method further comprises:
determining the urination disorder by the analysis device through the second preset method by using the urination time and the urination amount calculated by the analysis device.

10. The method of claim 9, wherein determining the urination disorder by the analysis device through the second preset method by using the urination time and the urination amount calculated by the analysis device comprises:
diagnosing the delayed urination symptom by the analysis device when the urination time is longer than a preset urination period of time.

11. The method of claim 5, wherein the wrist-worn wearable measurement device further comprises a temperature sensor and the sensor data obtained from the wrist-worn wearable measurement device further comprises temperature data detected by the temperature sensor, and wherein extracting, by the analysis device, the effective data related to the urination of the female subject further comprises:
filtering the sensor data to determine numerical values of the temperature data increasing during a time when the second sensor is moved from the second height to the first height which is lower than the second height, during the lapse of time.

12. The method of claim 3, wherein the preset angle is 100 degrees.

13. The method of claim 1, wherein the wrist-worn wearable measurement device further comprises a temperature sensor, and wherein sensor data obtained from the wrist-worn wearable measurement device further comprises temperature data for a temperature of the female subject.

* * * * *